United States Patent [19]
Franciskovich et al.

[11] Patent Number: 5,603,899
[45] Date of Patent: Feb. 18, 1997

[54] MULTIPLE COLUMN CHROMATOGRAPHY ASSEMBLY

[75] Inventors: Phillip P. Franciskovich, Brown Deer; David W. Walker, Milwaukee; Cynthia A. Mielke, Wauwatosa; David R. Boyer, West Allis, all of Wis.

[73] Assignee: Pharmacia Biotech, Inc., Milwaukee, Wis.

[21] Appl. No.: 421,633

[22] Filed: Apr. 12, 1995

[51] Int. Cl.$^6$ .................................................. G01N 30/02
[52] U.S. Cl. .......................... 422/100; 422/101; 422/102; 422/104; 436/177; 436/178; 436/809; 435/283.1
[58] Field of Search ................................. 422/100, 68.1, 422/101, 102, 104, 59, 70; 436/177, 178, 809; 435/296, 299, 300, 301, 311

[56] References Cited

U.S. PATENT DOCUMENTS

| | | | |
|---|---|---|---|
| D. 202,700 | 11/1965 | Cooke et al. | D16/1 |
| D. 226,846 | 5/1973 | Rosenburg | D16/1 |
| D. 246,466 | 11/1977 | Attree et al. | D24/31 |
| D. 283,162 | 3/1986 | Godsey | D24/31 |
| D. 303,011 | 8/1989 | Henry | D24/31 |
| D. 303,149 | 8/1989 | Anderson | D24/31 |
| 2,965,219 | 12/1960 | Rhodin | 206/1 |
| 3,107,204 | 10/1963 | Brown et al. | 195/103.5 |
| 3,356,462 | 12/1967 | Cooke et al. | 23/292 |
| 3,441,383 | 4/1969 | Moore et al. | 23/292 |
| 3,597,326 | 8/1971 | Liner | 195/139 |
| 3,649,464 | 3/1972 | Freeman | 195/140 |
| 3,674,198 | 7/1972 | Eberle | 233/26 |
| 4,135,660 | 1/1979 | Conn et al. | 233/26 |
| 4,154,795 | 5/1979 | Thorne | 422/99 |
| 4,215,198 | 7/1980 | Gordon | 435/31 |
| 4,426,295 | 1/1984 | Evans et al. | 210/772 |
| 4,435,293 | 3/1984 | Graham, Jr. et al. | 210/772 |
| 4,461,328 | 7/1984 | Kenney | 141/67 |
| 4,464,254 | 8/1984 | Dojki et al. | 210/136 |
| 4,468,974 | 9/1984 | Malinoff | 73/863.32 |
| 4,484,907 | 11/1984 | Sheeran, Jr. | 994/85 |
| 4,486,315 | 12/1984 | Teipel | 210/772 |
| 4,493,815 | 1/1985 | Fernwood et al. | 422/101 |
| 4,510,119 | 4/1985 | Hevey | 422/71 |
| 4,560,535 | 12/1985 | Bouchée | 422/102 |
| 4,565,100 | 1/1986 | Malinoff | 73/863.32 |
| 4,713,925 | 12/1987 | Kafkis | 53/432 |
| 4,761,379 | 8/1988 | Williams et al. | 435/296 |
| 4,775,629 | 10/1988 | Kuhl et al. | 435/299 |
| 4,787,988 | 11/1988 | Bertoncini et al. | 210/808 |
| 4,791,060 | 12/1988 | Chandler | 435/296 |
| 4,810,471 | 3/1989 | Wachob et al. | 422/103 |
| 4,832,842 | 5/1989 | Limb | 210/249 |
| 4,871,674 | 10/1989 | Matsui et al. | 422/102 |
| 4,874,691 | 12/1989 | Chandler | 435/7 |
| 4,895,706 | 1/1990 | Riot et al. | 422/104 |
| 4,927,604 | 5/1990 | Mathus et al. | 422/101 |
| 4,948,564 | 8/1990 | Root et al. | 422/101 |
| 4,956,298 | 9/1990 | Diekmann | 430/311 |
| 4,995,967 | 2/1991 | van Driessche | 210/94 |
| 5,084,246 | 1/1992 | Lyman et al. | 422/102 |
| 5,110,556 | 5/1992 | Lyman et al. | 422/101 |
| 5,141,719 | 8/1992 | Fernwood et al. | 422/101 |
| 5,227,137 | 7/1993 | Monti et al. | 422/102 |
| 5,273,718 | 12/1993 | Sköld et al. | 422/101 |
| 5,285,823 | 2/1994 | Honda | 141/7 |
| 5,310,527 | 5/1994 | Romanauskas et al. | 422/102 |
| 5,342,581 | 8/1994 | Sanadi | 422/101 |

*Primary Examiner*—Jill Warden
*Assistant Examiner*—Sharidan Carrillo
*Attorney, Agent, or Firm*—Quarles & Brady

[57] ABSTRACT

An apparatus, for simultaneously separating multiple samples into their constituents, includes a column manifold which has a plate with a plurality of apertures therethrough. A plurality of support tubes extend from the plate and each support tube has a passage in communication with one of the apertures. The column manifold also includes a fitting to which a vacuum source can the connected, thus enabling the apparatus to be used with both a centrifuge and a vacuum source. A separate separation column is removably received in each support tube and projects through the associated aperture. A collection plate has a plurality of wells arranged so that each well is aligned with a different support tube when the column manifold is placed against the collection plate. This alignment enables each well to receive material expelled from the separation column received in the corresponding support tube.

18 Claims, 3 Drawing Sheets

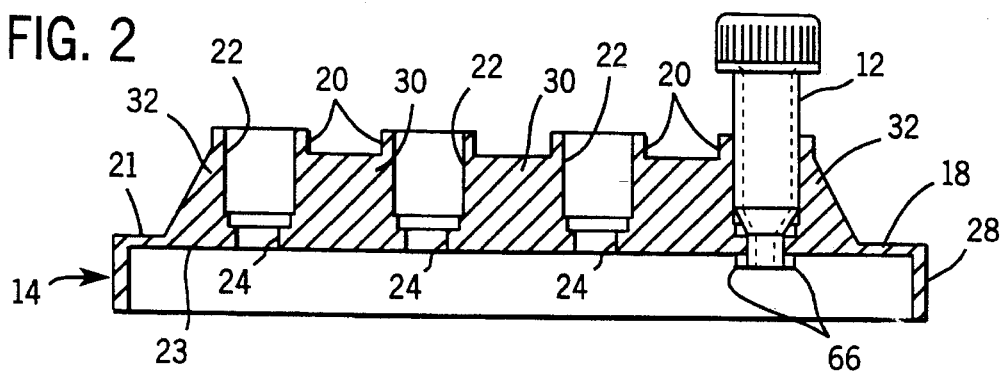
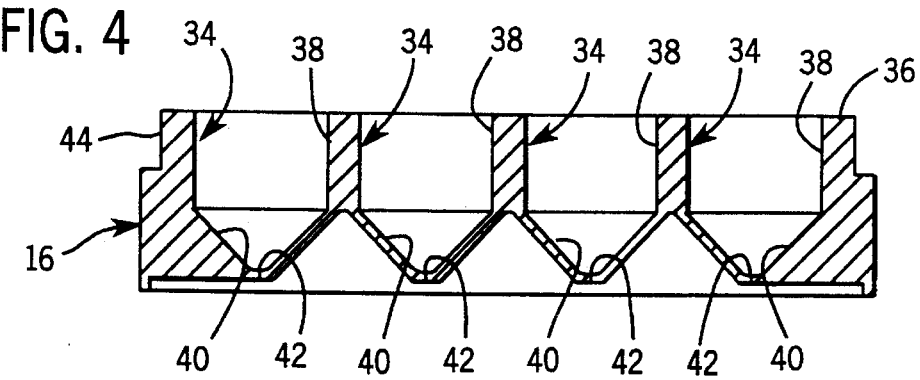
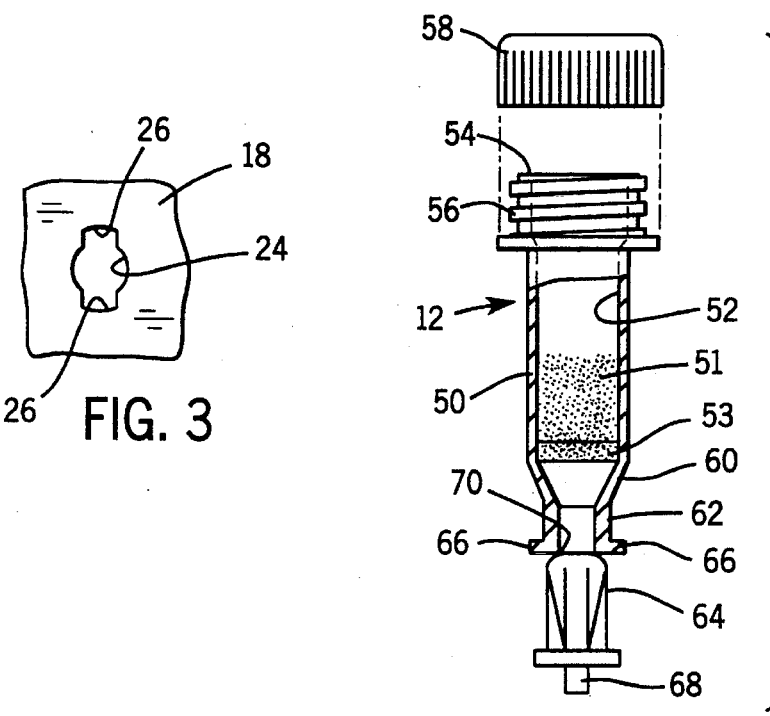

MULTIPLE COLUMN CHROMATOGRAPHY ASSEMBLY

BACKGROUND OF THE INVENTION

The present invention relates to chromatography columns used in separating constituents of chemical and biological samples; and more particularly to such apparatus in which sample material is drawn through the column by centrifugal force or vacuum.

Tubular columns containing a separation medium, such as a filtration matrix or an ion exchange material among other media, are frequently utilized in the biotechnology field to separate constituent materials from a sample. For example, this technique is used to separate DNA, which passes through the column, from lower molecular weight substances, which are retained in the separation medium. The particular material of the separation medium is selected to separate a specific constituent. One version of such a process is referred to as "spun-column chromatography" as the column is spun in a centrifuge so that the centrifugal force drives the sample through the separation medium. The constituents that pass completely through the column can be collected for further processing or analysis. The procedure may be repeated with wash or eluant steps to remove and collect the constituents contained in the separation medium.

Previous assemblies for spun column chromatography included a filter tube that contained a resin filtration matrix. This filter tube has an open first end through which the sample to be separated is introduced and through which solvents and reagents may be added at different steps of the process. A second open end of the filter tube fits into a centrifuging tube which has only one open end for receiving the filter tube and which serves as a collection vessel for constituents that pass through the filter tube. The assembled tubes are placed into a fixed angle or a swinging bucket holder at an end of a centrifuge rotor arm. After centrifuging, the tubes are separated and different sample constituents are contained in each one.

A laboratory often has a large number of different chemical or biological samples to be processed in this manner. However, handling individual tube assemblies for each sample is laborious and time consuming. Therefore, it is desirable to have a separation column apparatus that can facilitate the simultaneous processing of multiple samples.

Another previous technique for drawing the sample through the column created a vacuum at the second end of the column tube. This process requires a different collection vessel into which the column tube is placed wherein a vacuum source can be connected to the vessel in a manner that does not interfere with the collection of sample constituents that pass through the column. These vacuum devices typically had a single column. Other vacuum devices, such as that disclosed in U.S. Pat. No. 4,775,629, could process several column tubes at one time, but the material passing through the column was carried out of the device by the vacuum and could not be collected.

SUMMARY OF THE INVENTION

An object of the present invention is to provide apparatus for simultaneously separating a plurality of chemical and biological samples into their respective constituent components.

Another object is to provide such an apparatus which can be used with either a centrifuge and a vacuum source to drive the sample through the apparatus.

A further object of the present invention is to provide a collector which is designed to gather a separated constituent into a confined region for ease of removal.

These and other objects are fulfilled by an apparatus that comprises a column unit which preferably is formed by a manifold with a plurality of support tubes and a plurality of separation columns which are removably placed in the support tubes. Each separation column preferably has a tubular shape which tapers to a tip at one end to tightly mate with the support tube. A conventional chromatography or other separation medium for separating sample constituents is contained in each column.

A collection plate is placed adjacent to the column manifold and has a plurality of wells arranged so that each support tube is aligned with a different well. Thus the wells will receive material expelled from a separation column held in the corresponding support tube. A keying mechanism may be provided so that the column manifold and the collection plate can be assembled with the wells and support tubes properly aligned in only one orientation. This ensures that the user will be able to determine from which separation column in the column manifold a constituent in a well of the collection plate originated.

In the preferred embodiment of the column assembly, a coupling for a hose from a vacuum source is provided on the column manifold. The coupling facilitates use of vacuum to drive the sample through the columns and into the collection plate wells. Thus the same separation apparatus may be used with either a centrifuge or a vacuum source to process multiple samples simultaneously.

BRIEF DESCRIPTION OF THE DRAWINGS

FIG. 2 is a cross-section view taken along line 2—2 of FIG. 1;

FIG. 3 is a plain view of a keyed aperture in the column support plate in FIG. 1;

FIG. 4 is a cross-section view taken along line 4—4 in FIG. 1;

FIG. 5 is an exploded view of a column prior to use;

DETAILED DESCRIPTION OF THE INVENTION

Figure 1:
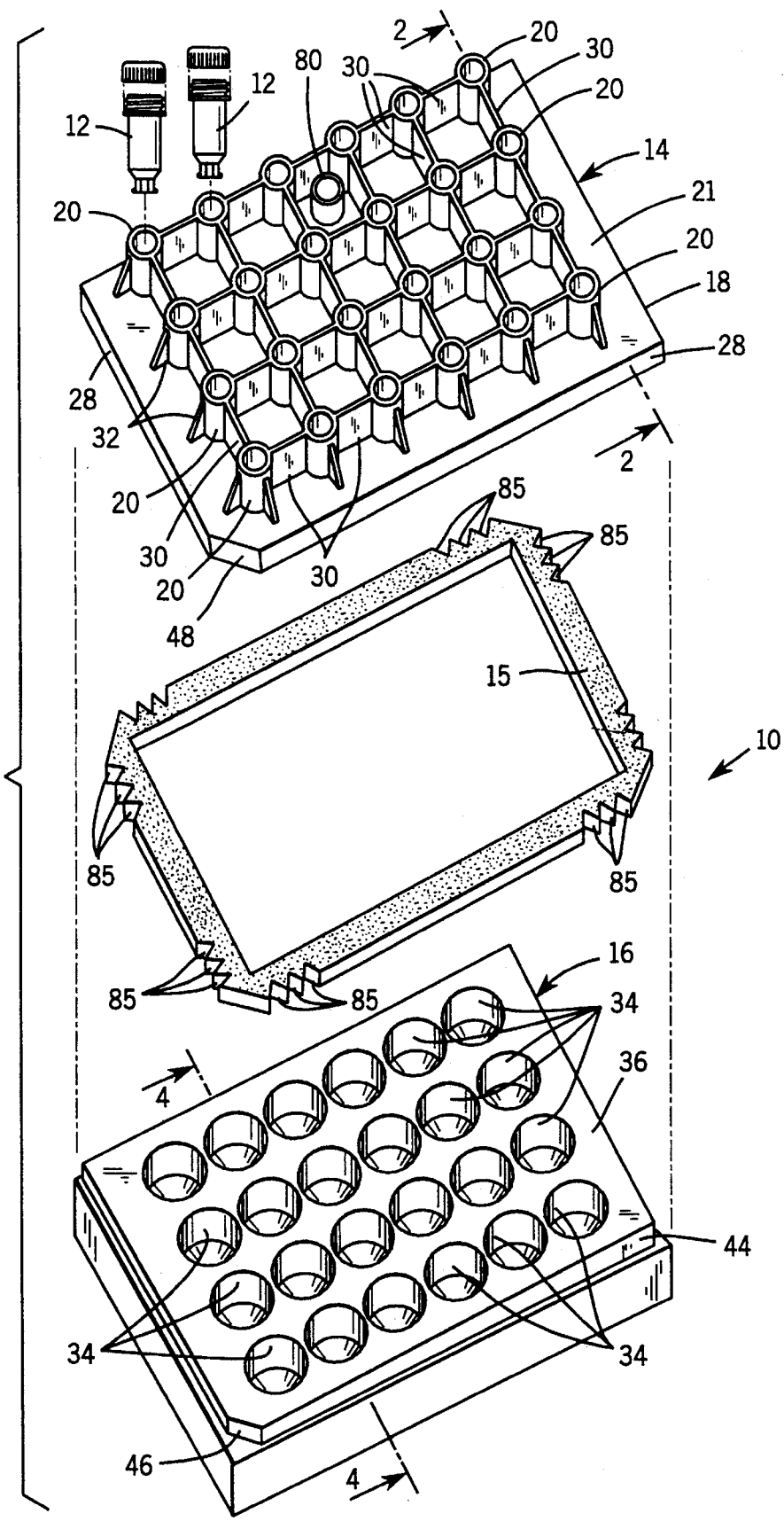
FIG. 1 is an exploded isometric view of a multiple column processing apparatus according to the present invention.

With initial reference to FIG. 1, a chemical or biological sample processing apparatus 10 includes a plurality of sterile separation columns 12 held within a column manifold 14 which rests on a collection plate 16 which may be sterile. The sample processing apparatus 10 when fully populated, contains twenty-four separation columns 12 located within support tubes 20 of the column manifold 14. However, in certain applications of the present apparatus which will be described subsequently, a lesser number of separation columns can be utilized when the full compliment of twenty-four separation columns is not required for processing.

Referring also to FIG. 2, the column manifold 14 includes a flat rectangular plate 18 having twenty-four support tubes 20 projecting from an upper major surface 21. Each support tube 20 has a tapered central passage 22 extending therethrough in communication with an aperture 24 through the plate 18. As shown in FIG. 3, each aperture 24 has a circular center portion with a pair of keyways 26 located on diametrically opposite sides of the aperture. As will be described, the keyways 26 provide a mechanism for locking the separation columns 12 in the support tubes. The twenty-four support tubes 20 are arranged in a six by four rectangular array on the plate 18, although other numbers of support tubes and array dimensions may be used. The rows and columns of the array may be identified with alphanumeric characters on the plate 18 to enable reference to a specific support tube. A support wall 30 extends upward from the plate 18 between adjacent tubes 20 to provide rigidity to the array. A triangular buttress 32 is coupled between each outer support tube and the upper surface 21 of column manifold plate 18 to further strengthen the array of support tubes 20. The corner support tubes have two such buttresses 32. A skirt-like flange 28 extends downward from the lower major surface 23 along the four edges of plate 18, in the orientation shown in FIG. 2.

The column manifold 14 rests on top of the collection plate 16 which is shown in detail in FIGS. 1 and 4. The collection plate 16 has a twenty-four wells 34 arranged in a six by four array on an upper surface 36 of the collection plate. Each well 34 has a cylindrical upper portion 38 with a conical lower portion 40 which tapers inward toward the bottom 42 of the well 34. The cross-sectional area of the cylindrical well portion 38 is significantly greater than the cross-sectional area of the aperture 24 through the plate of the column manifold 14. This size relationship aids in gathering material expelled from the associated separation column 12 and concentrating that material in the bottom region of the well.

When the column manifold 14 is assembled onto the collection plate 16, the skirt-like flange 28 on the column manifold fits into a recess 44 around the upper surface 36 of the collection plate 16. This engagement of the flange 28 within the recess 44 limits horizontal movement of the column manifold 14 and maintains each of the apertures 24 aligned over a separate well 34 in the collection plate 16. One corner 46 of the collection plate upper surface 36 is truncated and a corresponding corner 48 of the column manifold 14 is truncated in a similar manner. The truncated corners 46 and 48 provide a keying mechanism so that the column manifold 14 can be properly placed onto the collection plate 16 in only one orientation. Thus, the column manifold 14 cannot be rotated 180 degrees and still properly fit onto the collection plate 16. This ensures that the user will always be able to determine from which separation column 12 material was deposited into each well 34 of the collection plate. This reduces the possibility that the deposits in wells can be mismatched with the samples that were processed through the separation columns.

Referring to FIG. 5, each separation column 12 comprises a tubular body 50 with a central passage 52 extending therethrough. One end 54 of body 50 has external threads 56 which are used to fasten a threaded cap 58 to close the first end 54. The cap 58 has an internal O-ring (not shown) or other feature which provides a hermetic seal between the body 50 and the cap. Within passage 52 adjacent the tapered portion 60 of body 50 is a fixed filter 53, of polyethylene for example, which fills the entire diameter of the passage. Above the filter is a conventional chromatographic separation medium 51 having particles which entrap specific constituents of the sample material to be separated. Depending upon the separation process to be performed, the separation medium may be of the type commonly used for gel filtration, ion exchange, hydrophobic interaction, or affinity chromatography, for example.

The opposite end of body 50 has a tapered portion 60 which reduces the outer diameter of the tubular separation column 12 to a smaller end tube portion 62. A pair of diametrically opposed wing-like keys 66 project from the side of the end tube 66 at an end that is remote from the tapered portion 60. As will be described, these keys 66 cooperate with keyed aperture 24 in the column manifold 14 to provide a mechanism that locks the end tube 62 within a support tube 20. The need for the keys 66 and the keyed aperture 24 may be eliminated if the friction fit is sufficient to hold separation columns 12 in the support tubes 24. The passage 52 within the column body 50 extends through the end tube 62 and is closed by a break-away tip section 64. The user is able to break tip section 64 off the remainder of the tube body 50 at the junction between the tip section 64 and the end tube 62, thereby opening the passage 52 at that point. The remote end of the break-away tip section 64 has a cylindrical plug 68 that can be inserted to reseal the opening 70 of passage in the end tube 52 if desired at a subsequent processing step.

To use the separation column 12, the break-away tip section 64 is severed from the end tube 62 so as to open the lower end of the body 50. The separation column 12 is then inserted into one of the support tubes 20 in the column manifold 14 by pushing the separation column downward into the tapered support tube passage 22 creating a seal. The separation column 12 is orientated within passage 22 so that the wings 66 on the separation column align with the keyways 26 of the aperture 24 in the plate 18 as shown in FIGS. 2 and 3. The separation column 12 is pushed further inward so that the lower end of the separation column and the wings 66 pass through aperture 24. The separation column then is rotated so that the wings 66, which are now on the opposite of plate 18, are no longer aligned with the keyways 26 thereby locking the separation column 12 within the support tube 20. The separation column 12 can be removed from the column manifold 14 by reversing the assembly procedure. Alternatively, the wings 66 can be eliminated if the separation column 12 has a friction fit within the passage 22 of the support tube 20 which will hold the separation column in place during the processing. In either case, the smaller tip of the separation column 12 projects from the lower major surface of the column manifold 14 so that the material passing through the column does not contact the manifold. As a consequence, the column manifold 14 does not have to be sterilized in order to prevent contamination of the sample constituents and may be reused easily. Thus the present apparatus 10 provides a reusable column manifold 14 and disposable separation columns 12 and collection plate 16.

The same separation medium 51 may be present in all of the separation columns 12 so as to perform the same chromatographic procedure on all of the samples. Alternatively, the separation columns 12 may have different separation media 51, for example the separation columns in each row or column of the support tube array may have the same separation medium.

After all the separation columns 12 have been inserted, the column manifold 14 is placed on top of the collection plate 16 with the truncated corners 46 and 48 of the components aligned to ensure proper fit of the components. Depending upon the separation process being employed a membrane 55 shown in FIG. 7 can be placed between the column manifold 14 and the collection plate 16. Membranes of nitrocellulose, nylon and other materials are well known for attracting constituents of fluids passing therethrough. With the caps 58 removed, a pipette or syringe is used to introduce the samples to be separated into the top of each separation column 12. Thereafter, the caps 58 may be tightly placed on the separation columns, left off or loosely applied.

A pair of the assembled sample processing apparatus 10 are placed on opposite sides of a centrifuge rotor arm in swinging brackets designed to firmly hold the apparatus in an assembled state while centrifugation occurs. During the centrifuging process, a sample that has been placed in the upper portion of the separation column 12 is driven through the separation medium which entraps selected material in the sample. Other constituents of the sample pass out the opening in the end tube 62 and into well 34 in collection plate 16. The conical bottom portion 40 of the wells concentrates these constituents in the small bottom 42. Alternatively, a membrane 55 may be placed between the lower plate surface 23 of the column manifold 14 and the upper surface 36 of the collection plate 16 to introduce and additional means of separation.

Figures 6, 7:
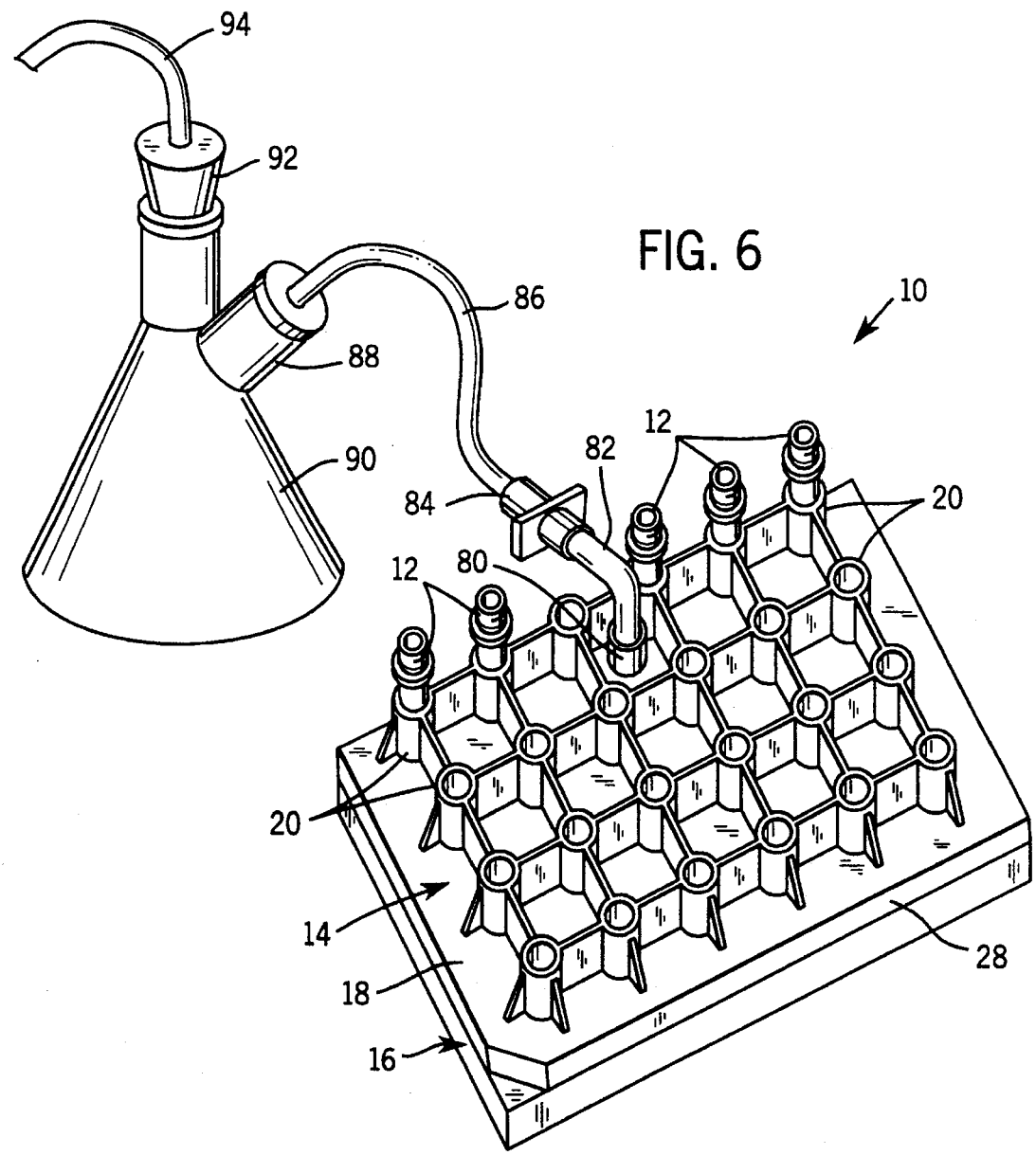
FIG. 6 is an isometric view of the multiple column processing apparatus connected to a vacuum source.
FIG. 7 shows a membrane which may be used in the separation process performed with the multiple column processing apparatus.

As shown in FIG. 6, the present processing apparatus 10 also can be used with a vacuum source to draw the samples through the separation columns. A nipple 80 extends from the upper surface of the column manifold plate 18. The nipple is located between the first and second rows of support tubes 20 from one edge of the plate 18 and between the third and fourth columns of support tubes. This location centrally positions the nipple at a point in which connection of a vacuum source will not interfere with introducing material into the separation columns 12 inserted into the support tubes as will be described. The nipple 80 has a tapered orifice which communicates with a passage through the column manifold plate 18.

A vacuum source is attached to the nipple 80 using an tubular elbow 82 which has a standard fitting at each end. Alternatively, the one end of the elbow 82 could be designed to sealingly fit into an unused support tube 20, in which case nipple 80 would not have to be provided. The other end of elbow 82 is received in a fitting 84 at an end of a hose 86 which is connected at the opposite end to the side arm 88 of a glass side-arm flask 90. A rubber stopper 92 seals a top opening of the flask 90 with another hose 94 from a vacuum source (not shown) connected to an passage through the stopper.

To set up the processing apparatus 10 for vacuum use, the elbow 82 first is connected to the nipple 80 on the column manifold 14. Twenty-four separation columns 12 then are inserted into the support tubes 20 in the same manner as described with respect to the centrifuge technique. Although for the centrifuge technique some of the support tubes 20 may be left vacant, a separation column 12 or a plug now has to be placed in each support tube 20 even if all twenty-four separation columns will not be used for processing samples. This closes all of the support tubes to prevent excessive vacuum leakage. In order to simplify the illustration in FIG. 6, only some of the support tubes 20 are shown with separation columns 12.

The column manifold 14 then is placed onto the collector plate 16 as shown in FIG. 6. For the vacuum technique, the annular gasket 15 shown in FIG. 1 is placed between the column manifold 14 and the collector plate 16 to provide a relatively air-tight seal. This gasket 15 is not required when a centrifuge is employed to drive the sample through the chromatographic separation medium. To create an air pressure differential within the apparatus, the lower major surface 23 of the column manifold plate 18 serves as a sealing surface against which the gasket 15 abuts. The gasket 15 has a rectangular size that fits within the flange 28 which extends around the column manifold 14. The corners of the gasket are truncated so that any one of them can be received in the truncated corner 48 of the column manifold 14. Three triangular notches 85 are cut into the edges of the gasket on each side of the four corners. The tips between each notch 85 project slightly beyond the straight section of the side edge. When the gasket 15 is placed within the column manifold flange 28, those points are compressed and exert force against the flange to hold the gasket in places Making the gasket slightly larger than the distance between opposite flanges undesirably causes the gasket to buckle which can interfere with the sealing ability. Instead the projecting points 85 flatten into the adjacent notches to hold the present gasket in place without buckling. The central opening of the gasket 15 creates a space between the column manifold 14 and the collector plate 16 which enables all of the wells to be evacuated.

The samples then can be introduced into the separation columns 12 either from a single pipette or a multiple pipette. Because elbow 82 is below the tops of the adjacent separation columns and exits to the side of the column manifold 14, the elbow does not interfere with the introduction of samples or eluent into the separation columns 12. Although the illustrated location of the nipple 80 provides this feature, the nipple can be located at other positions on the column manifold 14. The caps 58 may be left removed from the separation columns 12 as shown in FIG. 6 or loosely placed thereon.

The hose 86 of the vacuum system then is connected to the elbow 82 and the vacuum is applied to the apparatus 10. The vacuum draws the samples through the separation columns 12 with the material that passes entirely through the separation columns being deposited into the associated well 34 of the collection plate 16. The flask 90 serves as a trap for any material that is inadvertently drawn into the hose 86 and prevents such material from contaminating the vacuum source. In addition a standard filter may be coupled between the elbow 82 and the hose 86 to limit the transmission of material from the sample processing apparatus 10. Instead of using a vacuum to draw the sample through the separation column, a positive pressure can be applied to openings at the tops of the columns to drive the sample downward through the separation medium. In this variation, a hood-like housing would be placed over the column manifold 14 and sealed in an air-tight manner to the upper major surface 21 of plate 18. The housing then is pressurized with air to create an air pressure differential within the separation apparatus.

We claim:

1. An assembly for separating a sample into constituents, said assembly comprising:

a single piece column manifold having a plate with first and second surfaces, a plurality of support tubes connected in a two dimensional array to the first surface of the plate, a plurality of walls each of which is connected to the first surface of the plate and to the plurality of support tubes wherein each support tube is connected to at least two walls, a fitting attached to the first surface of the plate for connecting a vacuum source to the column manifold;

a plurality of tubular separation columns, wherein each one of the plurality of tubular separation columns is removably received in a different one of the plurality of support tubes; and a single piece collection plate with a plurality of wells arranged in a pattern wherein each support tube is aligned with a different well when said column manifold is placed against said collection plate to collect material expelled from at least one separation column received in a support tube.

2. The assembly as recited in claim 1 wherein each one of said plurality of tubular separation columns contains a separation medium for separating constituents from the sample.

3. The assembly as recited in claim 1 further comprising a gasket between said column manifold and said collection plate.

4. The assembly as recited in claim 3 wherein said gasket comprises an annular sheet with an edge extending there around, wherein the annular sheet as a plurality of notches spaced along the edge.

5. The assembly as recited in claim 1 wherein each of the plurality of wells in said collection plate has a conical bottom section.

6. The assembly as recited in claim 1 further comprising a keying mechanism which defines a single orientation of the plurality of support tubes with the plurality of wells of said collection plate.

7. The assembly as recited in claim 1 wherein each of the plurality of tubular separation columns has a key; and a keyway which is constructed to retain with each of said plurality of support tubes, wherein the key of a given tubular separation column cooperates with a keyway to lock the given tubular separation column within one of the plurality of support tubes.

8. The assembly as recited in claim 1 wherein each of the plurality of tubular separation columns comprises a body with a first end, a second end and a central passage having a first opening at the first end, and a tip section attached to the second end of the body in a manner that allows a user to break the tip section away from the body to provide a second opening of the central passage.

9. The assembly as recited in claim 8 wherein the tip section has a plug projecting therefrom for closing the second opening after the tip section has been broken off the body.

10. An apparatus for separating samples into constituents, said apparatus comprising:

a single piece column manifold having a plate with first and second surfaces and a plurality of apertures through the plate, and having a plurality of support tubes extending from the first surface of the plate wherein each support tube has a passage therethrough in communication with one of the apertures of the plate, and a plurality of walls each of which is connected to the first surface of the plate and to two of the plurality of support tubes;

a plurality of tubular separation columns, each one of which is removably received in a different one of the plurality of support tubes; and a collection plate located against the single piece manifold and having a plurality of wells formed in the collection plate and arranged in a pattern wherein each support tube is aligned with a different well to collect material expelled from each one of the separation columns received in each one of said support tubes.

11. The apparatus recited in claim 10 wherein the plurality of support tubes is arranged in a two dimensional array with each support tube connected to at least two of the plurality of walls.

12. The apparatus as recited in claim 11 wherein the support tubes which are located along a perimeter of the two dimensional array have a buttress connected to the first surface of the plate.

13. The apparatus as recited in claim 10 wherein said column manifold further comprises a flange extending around the plate for engaging said collection plate to limit movement between said column manifold and said collection plate.

14. The assembly as recited in claim 10 further comprising a gasket between said column manifold and said collection plate.

15. The assembly as recited in claim 14 wherein said gasket comprises an annular sheet with an edge extending there around, wherein the annular sheet as a plurality of notches spaced along the edge.

16. The apparatus as recited in claim 10 further comprising a keying mechanism which defines a single orientation of the passages in the column manifold with the plurality of wells of said collection plate.

17. The apparatus as recited in claim 10 wherein each of the plurality of wells in said collection plate has a conical bottom section.

18. The apparatus as recited in claim 10 wherein said column manifold further comprises a coupling mounted on the plate for attaching a vacuum source to said column manifold.

* * * * *